United States Patent [19]
Koomruian, Jr.

[11] Patent Number: 6,000,534
[45] Date of Patent: Dec. 14, 1999

[54] CONTACT LENS DISINFECTING DEVICE AND DISINFECTION SYSTEM

[75] Inventor: Charles Koomruian, Jr., Costa Mesa, Calif.

[73] Assignee: Allergan Sales, Inc., Irvine, Calif.

[21] Appl. No.: 08/698,743

[22] Filed: Aug. 16, 1996

[51] Int. Cl.⁶ ................................................. B65D 51/16
[52] U.S. Cl. ........................ 206/5.1; 134/901; 220/371; 422/300
[58] Field of Search ................................. 206/5.1, 205, 439, 206/484.1; 134/901; 220/367.1, 371; 422/292, 300

[56] References Cited

U.S. PATENT DOCUMENTS

| | | | |
|---|---|---|---|
| 4,136,796 | 1/1979 | Dubois et al. ........................... | 220/371 |
| 4,396,583 | 8/1983 | Leboeuf . | |
| 4,637,919 | 1/1987 | Ryder et al. . | |
| 4,750,610 | 6/1988 | Ryder ........................................ | 206/5.1 |
| 4,765,499 | 8/1988 | Von Reis et al. ......................... | 220/371 |
| 4,889,693 | 12/1989 | Su et al. .................................... | 206/5.1 |
| 5,143,104 | 9/1992 | Iba et al. ................................... | 134/901 |
| 5,250,266 | 10/1993 | Kanner ..................................... | 134/901 |
| 5,283,053 | 2/1994 | Kamiya et al. ........................... | 134/901 |
| 5,353,949 | 10/1994 | Seibert et al. ............................ | 220/371 |
| 5,366,078 | 11/1994 | Braun ....................................... | 134/901 |
| 5,388,686 | 2/1995 | Kanner et al. ............................ | 206/5.1 |

*Primary Examiner*—Paul T. Sewell
*Assistant Examiner*—Luan K. Bui
*Attorney, Agent, or Firm*—Carlos A. Fisher; Martin A. Voet; Robert J. Baran

[57] ABSTRACT

The present invention provides a device for disinfecting and storing a contact lens comprising a container, a lens holding means for supporting a contact lens, a cap for sealably covering the open end of the container and a gas-permeable, liquid-impermeable membrane fixed to the internal surface of the appliance and positioned to cover all apertures in the appliance to allow oxygen to escape from the device but preventing liquid from escaping from the device when an oxidative disinfectant is used in the appliance.

4 Claims, 1 Drawing Sheet

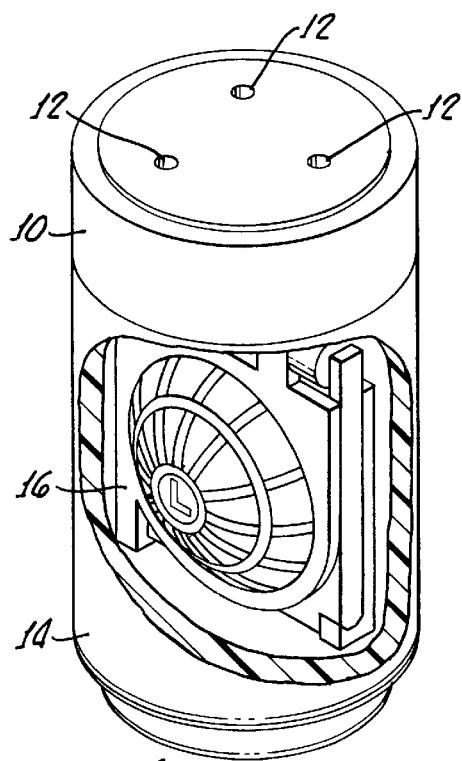
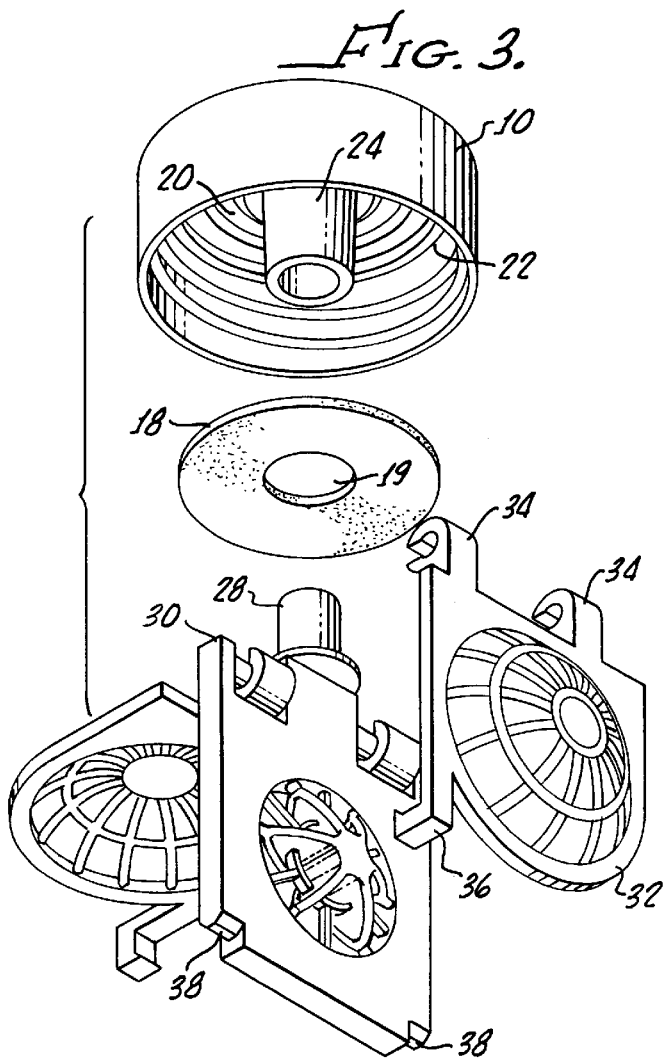
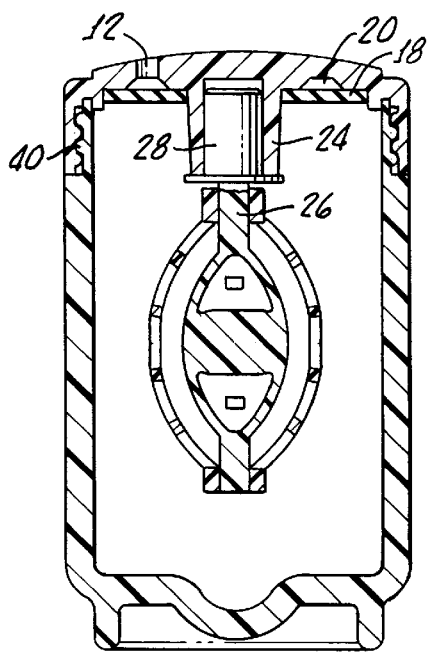
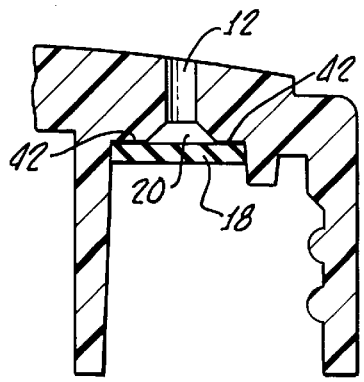
FIG. 1.
FIG. 2.
FIG. 3.
FIG. 4.

CONTACT LENS DISINFECTING DEVICE AND DISINFECTION SYSTEM

BACKGROUND OF THE INVENTION

The present invention concerns an improved contact lens disinfecting device.

Use of hydrogen peroxide for the chemical sterilization or disinfecting of soft contact lenses is well-known in the art. Such lenses are generally disinfected inside particularly-crafted contact lens holders. For example, U.S. Pat. No. 4,637,919 discloses a lens disinfecting appliance with an improved venting feature for use with oxidative disinfectants. The venting feature in the '919 patent is a filter cartridge inserted into an aperture. This allows oxygen produced by decomposing hydrogen peroxide to escape from the device.

The purpose for venting in a contact lens disinfecting appliance is to allow oxygen to escape. Hydrogen peroxide is an oxidative disinfectant, that is, as part of the disinfection process, the hydrogen peroxide breaks down into water and oxygen. For such disinfection systems, the appliance containing the lenses and the disinfectant must be designed to allow oxygen to escape from the appliance or the appliance might explode due to the build up of vapor pressure.

Other attempts to solve the problem of providing a contact lens disinfecting device which can vent the oxygen produced by decomposing hydrogen peroxide include U.S. Pat. No. 4,396,583. In the '583 patent, a contact lens disinfection appliance which can vent oxygen is disclosed. In the appliance a gas-permeable, liquid-impermeable membrane is loosely fitted inside a space in a cap of the device. The membrane is positioned between the disinfecting chamber and apertures located in the cap. The apertures in the cap allow gas which has passed through the membrane to escape.

Unfortunately, neither the invention disclosed in the '583 patent nor in the '919 patent adequately solves the problem of venting the oxygen created during hydrogen peroxide decomposition while providing a leak-proof and non-clogging appliance. The '919 patent provides an appliance with minimal surface area to allow oxygen to escape. In addition, leakage is a potential problem as the filter cartridge is not adequately secured inside the aperture into which it is placed. Moreover, the filter cartridge would have a tendency to clog because of its minimal surface area.

The appliance disclosed in the '583 patent is also inadequate because it provides a membrane which can be easily dislodged. Since this membrane in the appliance in the '583 patent can be easily dislodged, the appliance is likely to leak.

The present invention solves the problems of the prior art by providing a contact lens disinfecting appliance with a gas-permeable, liquid-impermeable member fixed securely thereto which can properly and adequately vent oxygen created during hydrogen peroxide decomposition without clogging or leaking.

SUMMARY OF THE INVENTION

The present invention provides a device or appliance for disinfecting and storing contact lenses, the device comprising a container including an open end, a lens holding means for supporting at least one contact lens within the container, a cap for sealably covering the open end of the container wherein the cap includes an internal and external surface and has at least one aperture to serve as a vent and a gas-permeable, liquid-impermeable member, the member fixed to the internal surface of the cap and positioned so as to cover any vents.

The present invention further provides a contact lens disinfection system, the system comprising a lens holding appliance including a container with an open end, a cap for sealably covering the open end, means for holding at least one contact lens and a vent. The vent has at least one aperture and a gas-permeable, liquid-impermeable membrane wherein the membrane is fixed to the appliance and positioned to cover any aperture. The system further includes an effective disinfecting amount of an oxidative disinfectant.

BRIEF DESCRIPTION OF THE FIGURES

FIG. 1 provides a frontal view of an embodiment of the present invention with a portion of the container cut away to exhibit the lens holding baskets;

FIG. 2 provides a cross-sectional view of the embodiment of present invention in FIG. 1;

FIG. 3 is an exploded perspective view of the embodiment of the present invention in FIG. 1; and FIG. 4 is a partial sectional view of an assembled container cap with the membrane welded thereto.

DETAILED DESCRIPTION OF THE INVENTION

The present invention can be used with all contact lenses such as conventional hard, soft, rigid gas permeable, and silicone lenses. The invention is preferably employed with soft lenses, such as those commonly referred to as hydrogel lenses. Hydrogel lenses are typically prepared from monomers, such as hydroxyethylmethacrylate, vinylpyrrolidone, glyceryl-methacrylate, methacrylic acid or acid esters and the like. Such hydrogel lenses include disposable, extended wear and continuous wear lenses. Hydrogel lenses typically absorb significant amounts of water, such as in the range of about 38 to about 80 percent by weight or more. In addition, the pores of such hydrogel lenses have diameters of about 30–90 Å.

The present invention provides a device for disinfecting and storing a contact lens comprising a container including an open end, a lens holding means for supporting at least one contact lens within the container, a cap for sealably covering the open end of the container wherein the cap having an internal and external surface and at least one aperture to serve as a vent and a gas-permeable, liquid-impermeable member, the member secured to the internal surface of the cap and positioned so as to cover any vent.

In a preferred embodiment of the present invention the gas-permeable, liquid-impermeable member is welded to the internal surface of the cap. In another preferred embodiment of the present invention the gas-permeable, liquid-impermeable member includes a gas-permeable, liquid-impermeable membrane.

In a further embodiment of the present invention, the cap may be threadedly secured to the container body. Preferably, the container and cap of the present invention may be sealably secured without a gasket. Use of gasketless seals are well-known to those of ordinary skill in the art.

In another preferred embodiment of the present invention, the lens holding means for supporting at least one contact lens within the container comprises a set of baskets fixed to a basket supporting frame. Such baskets are well-known to those of ordinary skill in the art. Preferably, the gas-permeable, liquid-impermeable member has an internal void through which passes the basket-type lens holder, the edge of the gas-permeable, liquid-impermeable member along the void being secured to the internal surface of the cap such that the device does not leak. In a preferred embodiment, the member is donut shaped, providing an inside edge which defines the circumference of the internal void. The member also provides an outside edge. In a preferred embodiment, both edges of the gas-permeable, liquid-impermeable member are welded to the internal surface of the cap. In another embodiment of the present invention, the welds are located substantially around the apertures only.

The present invention provides a device having at least one aperture therein for use in disinfecting and storing a contact lens with a liquid, oxidative disinfectant, the device comprising a container including an open end, a lens holding means for supporting at least one compact lens, a cap for sealably covering the open end of the container, and a gas-permeable, liquid-impermeable member fixed to an internal surface of the appliance and positioned to cover all apertures. In this embodiment of the present invention, liquid oxidative disinfectant does not leak from the appliance when the top sealably covers the opening. But oxygen may escape the device through the gas-permeable, liquid-impermeable member and then through the aperture.

The present invention provides a contact lens disinfection system, the system comprising a lens-holding appliance including a container with an open end, a cap for sealably covering the open end, means for holding at least one contact lens and a vent. The vent has at least one aperture and a gas-permeable, liquid-impermeable membrane, wherein the membrane is fixed to the internal surface of the cap and positioned to cover any aperture and an effective disinfecting amount of an oxidative disinfectant. In a preferred embodiment of the present invention, the membrane is welded to the appliance.

Particularly useful oxidative disinfectant components are hydrogen peroxide or one or more other peroxide-containing compounds, for example, one or more other peroxides. Precursors to chlorine dioxide, such as stabilized purite, are also effective.

For hydrogen peroxide, a 0.5% (w/v) concentration, for example, in an aqueous liquid medium, is often effective as a disinfectant component. It is preferred to use at least about 1.0% or about 2.0% (w/v) hydrogen peroxide which concentrations reduce the disinfecting time over that of the 0.5% (w/v) peroxide concentration. No upper limit is placed on the amount of hydrogen peroxide which can be used in this invention except as limited in that the oxidative disinfectant component should have no substantial detrimental effect on the contact lens being treated or on the eye of the wearer of the treated contact lens. An aqueous solution containing about 3% (w/v) hydrogen peroxide is very efficacious.

So far as other peroxides are concerned, they should be used in effective disinfecting concentrations.

When an oxidative disinfectant is used in the present invention, preferably a reducing or neutralizing component in an amount sufficient to chemically reduce or neutralize substantially all of the oxidative disinfectant, for example, hydrogen peroxide, is employed.

Neutralizing components are well known to those of skill in the art and include catalase. Preferably, a non-bovine derived form of catalase is utilized. Preferably, a catalase produced by *Aspergillus niger* or *Micrococcus luteus* is used. Use of such catalases is disclosed in U.S. Pat. Nos. 5,362,647 and 5,521,091.

FIG. 1 provides a cap 10, the cap characterized by at least one aperture 12. FIG. 1 provides three such apertures. This is the preferred embodiment. A container 14 is also provided to which the cap 10 is securably attached. FIG. 1 provides a portion of the container 14 cut-away to show the lens-holding baskets 16.

FIG. 2 provides a cross-sectional view of the present invention. It provides a membrane 18 positioned such that it covers aperture 12. The membrane is placed within a race 20, the race 20 created by the positioning of the lens-holding basket frame 26 inserted inside a lens basket frame mounting receptacle 24 and the seal abutment 22. The lens basket supporting frame 26 is supported by a lens basket frame mount 28 which is inserted inside the lens basket frame mounting receptacle 24.

FIG. 3 provides an exploded perspective of the present invention whereby cap 10 is positioned to receive membrane 18 within the race 22. The membrane characterized by an internal void 19 which is of a size sufficient to allow the membrane 18 to avoid interference with the lens basket frame mounting receptacle 24 such that it can rest directly within the race 20 where it can be secured to the race 20 via gluing, welding or other well-known securing method.

FIG. 3 further provides the basket supporting frame which consists of the lens basket frame mount 28 and the axially-aligned gudgeons 30 upon which the snap-fitting 34 of the opposed lens covers 32 are attached. The opposed lens covers 32 can then be swung down to cover the opposed convex lens receiving surface 27 and secured to the basket supporting frame 26 with a claw 36 which snaps over the boss 38. FIG. 3 further provides threads 40 for securably attaching the cap 10 to the container 14.

FIG. 4 provides a cross-sectional view of the present invention. In particular, it provides a cross-sectional view of the membrane 18 welded 42 to the cap 10. The figure provides that the membrane 18 is positioned over the aperture 12 such that only gas and not liquid escapes from the aperture 12.

The subject invention may be produced from presently-available materials, most of which are plastic. The container or vial may be made from numerous plastic but preferably is made from clear acrylic. Preferably, the accrylic model CM-207 produced by Chi Mei of Taiwan. The cap and stem is preferably made from acrylonitrile-butadiene-styrene ("ABS"). Preferably, model ABS Custom 248 White 2002 produced by Bayer Polymer Division of Addyston, Ohio is used. Preferably, one of the baskets is also preferably produced from this material. The other basket is preferably produced from ABS Custom 248 Blue 58479, also provided by Bayer Polymer Division from Addyston, Ohio.

With respect to the membrane, preferably it is comprised of polytetrafluoroethylenes (PTFE). The pore size can vary between 0.01 μm to 100 μm. Preferably the pore size is 0.45 μm. A particular source of PTFE is W. L. Gore Corporation of Elkton, Md. which makes the Goretex® brand of PTFE.

With respect to fixing the membrane to the cap, gluing or welding may be used. Preferably the membrane is welded to the cap. In a preferred embodiment the membrane was welded ultrasonically to the cap by Performance Systematix, Inc. of Caledonia, Mich.

To use the appliance of the present invention, the lens holding baskets 16 receive contact lenses that are held in place by the opposed lens covers 32. A hydrogen peroxide sterilizing solution as described hereinabove, is then poured into the open end of the container 14. The cap 10 is then securably attached to the container. As the hydrogen peroxide decomposes into water and oxygen, the oxygen will proceed through the gas-permeable, liquid-impermeable membrane 18 and through one of the apertures 12 to escape from the appliance. However, under normal operating conditions liquid will not leak through the membrane nor through the welds of the membrane which bonds the membrane to the cap 10. As provided above, the catalyst may be provided before or after the hydrogen peroxide sterilizing solution has been added and the lenses disinfected, the catalyst used to destroy any residual hydrogen peroxide.

The result is a contact lens which is adequately disinfected and done so in an appliance which does not leak under normal operating conditions and is safe to the user.

Various patents and references were referred to in the subject patent application. All such patents and references are hereby incorporated by reference.

I claim:

1. A device for disinfecting and storing a contact lens comprising:

a container including an open end;

a lens holding means for supporting at least one contact lens within the container;

a cap for sealably covering the open end of the container wherein the cap includes internal and external surfaces and has at least one aperture to serve as a vent, the lens holding means is secured to the internal surface of the cap; and a gas-permeable, liquid-impermeable membrane having an internal void through which passes the lens holding means, the membrane welded to the internal surface of the cap and positioned so as to cover any vent and the edge of the gas-permeable, liquid-impermeable membrane along the internal void is welded to the internal surface of the cap.

2. The device of claim 1, wherein the cap is threadedly secured to the container body.

3. The device of claim 1, wherein the container and cap are sealably secured without a gasket.

4. The device of claim 1, wherein the lens holding means comprises a lens holding basket apparatus.

* * * * *